United States Patent [19]

Chung, deceased

[11] Patent Number: 4,528,352

[45] Date of Patent: Jul. 9, 1985

[54] RTV SILICON COMPOSITIONS AND PROCESSES

[75] Inventor: Rack H. Chung, deceased, late of Clifton Park, N.Y., by Betsy A. Chung, executrix

[73] Assignee: General Electric Company, Waterford, N.Y.

[21] Appl. No.: 542,842

[22] Filed: Dec. 2, 1983

Related U.S. Application Data

[62] Division of Ser. No. 338,518, Jan. 11, 1982, Pat. No. 4,424,157.

[51] Int. Cl.³ .............................................. C08G 77/06
[52] U.S. Cl. ..................................... 528/18; 524/860; 528/21; 528/33; 528/34; 528/901
[58] Field of Search ............... 528/18, 21, 34, 33, 528/901; 524/860

[56] References Cited

U.S. PATENT DOCUMENTS

| | | | |
|---|---|---|---|
| 4,012,375 | 3/1977 | Hahn | 528/34 |
| 4,347,336 | 8/1982 | Homan et al. | 528/34 |
| 4,360,631 | 11/1982 | Hahn | 528/34 |

*Primary Examiner*—Melvyn I. Marquis

[57] ABSTRACT

Substantially silanol-free, alkoxy functional RTV silicone rubber composition. The silanol and alkoxy groups in the composition are scavenged by the use of scavenging leaving groups which are present either in the cross-linking agent or in a separate compound. The scavenging leaving group in the instant composition is a heterocyclic amide functional group.

36 Claims, No Drawings

RTV SILICON COMPOSITIONS AND PROCESSES

This application is a division, of application Ser. No. 338,518, filed Jan. 11, 1982, now U.S. Pat. No. 4,424,157.

BACKGROUND OF THE INVENTION

The present invention relates to RTV compositions and more particularly, the present invention relates to the preparation and utilization of novel cross-linking agents and scavengers in the production of fast-curing, non-corrosive RTV compositions.

RTV silicone compositions are widespread and are utilized to produce sealants, molds for the production of molded parts, gasketing materials, etc. (RTV in this application refers to room temperature vulcanizable.) There are two types of RTV compositions: one is the one-component or one-package type; and the other is the two-component or two-package type. Examples of early one-component types are the ones, for instance, disclosed in Ceyzeriat U.S. Pat. No. 3,133,891 and Brunner U.S. Pat. No. 3,035,061. These patents disclose as the basic ingredients a silanol terminated diorganopolysiloxane polymer as the base polymer, an acyloxy functional silane as the cross-linking agent and a metal salt of a carboxylic acid as the condensation catalyst. As the Brunner patent notes there was formed in such compositions a diorganopolysiloxane polymer which had acyloxy functional terminal groups. Such composition was packaged in the substantial absence of moisture in a moisture proof package. When it was desired to use the composition, the seal on the package was broken and the composition was applied such that upon exposure to atmospheric moisture the acyloxy groups hydrolyzed to cross-link the polymer and form a silicone elastomer, with final cure taking place in anywhere from 24 to 72 hours. There was placed in the composition a metal salt of a carboxylic acid as a condensation catalyst. Preferably, such metal salt was a tin salt.

One disadvantage in such a composition is that it released acetic acid upon curing which was somewhat corrosive and gave off a somewhat unpleasant odor. There were various additives and other ingredients formulated into such compositions such as self-bonding additives and various other types of flame retardant additives. As time went on, various types of one-component RTV compositions were invented and produced, that is, compositions that were amine functional, that is the cross-linking agent was amine functional or ketoxime-functional or amide-functional, etc. However, there was a constant search to find a one-component RTV composition that is non-corrosive, that is, that the composition did not give off any corrosive by-products upon curing, and is fast curing.

It is important to note that there was also some development work in the two package or two-component area of RTV compositions. One, for instance, is disclosed in Nitzsche U.S. Pat. No. 3,127,363 which comprises mixing a polyalkoxysilane such as tetraethylsilicate or partial hydrolysis product thereof with the silanol end-stopped diorganopolysiloxane base polymer in the presence of a metal salt of a carboxylic acid. Although such composition was not corrosive and had fast-curing properties, nevertheless it did not have a sufficient shelf life after it was mixed. That is, the composition after it was mixed, had a short shelf life. It had to be used almost immediately. Accordingly, the composition could not be mixed and packaged as a single package and utilized as such. It had to be manufactured and sold in two components and then the worker in the field would mix the two components and apply them in accordance with the instructions. Not only were the instructions not always followed carefully in the preparation and application of such compositions, but also the labor involved increased the cost of utilizing such RTV compositions.

The disclosure of Nitzche et al U.S. Pat. No. 3,065,194 should be noted, in that this disclosure taught that a one-component RTV composition could be made from alkoxy end-block diorganopolysiloxane base polymer or an alkylortho silicate cross-linking agent and a tin soap as a curing catalyst. However, the disclosure noted that extreme drying procedures had to be carried out to see to it that a dry composition was prepared and that even with such a drying cycle in the preparation of the composition, the composition still had a relatively short shelf life. However, there were further formulations to make the two-component of Nitzsche et al one-component. Weyenberg U.S. Pat. No. 3,334,067, Cooper et al U.S. Pat. No. 3,542,901, Smith et al U.S. Pat. Nos. 3,689,454 and 3,779,986, disclose producing a one-component, non-corrosive, RTV silicone composition comprising a base silanol end-stopped polymer and an alkoxy cross-linking agent which preferably was methyltrimethoxysilane and condensation catalysts. These patents disclose the preferred type of condensation catalyst as various types of titanium chelate catalysts. The preferred condensation catalysts were titanium chelate catalysts such as that of Smith et al. U.S. Pat. Nos. 3,689,454 and 3,779,986 and to a lesser extent that of the Weyenberg patent which catalysts were effective in producing a low modulus, non-corrosive, one-component RTV composition which cured the composition completely but at a slow rate. However, the difficulty was that the tack-free time of such compositions was extended after storage for periods of time as small as five hours. Accordingly, such compositions were not fast curing, and various modifications had to be made such that they would cure at a sufficiently acceptable rate after being stored for periods of time of one year or more after manufacture. Such disclosures such as Weyenberg and Smith et al, went on the premise that the alkoxy-functional cross-linking agent was a desirable type of cross-linking agent in the production of a one-component system even though workers skilled in the art were not able to make an RTV composition that was sufficiently fast-curing and had shelf stability. Early work in this area of making such compositions shelf stable and having a sufficient cure rate as well as being non-corrosive is evidenced by the work disclosed in Brown et al U.S. Pat. No. 3,122,522 and Brown et al, U.S. Pat. No. 3,161,614 or U.S. Pat. No. Re. 29,760. In the latter patents Brown disclosed a polyalkoxy terminated diorganopolysiloxane polymer where this polymer was disclosed alone or in combination with a curing catalyst. However, even this polymer as disclosed in Brown et al, U.S. Pat. No. Re. 29,760 was not suitable as an RTV composition since it was not sufficiently fast-curing in the presence of most catalysts. It was with the development of the titanium chelate catalysts of Weyenberg, U.S. Pat. No. 3,334,067 and Smith et al, U.S. Pat. Nos. 3,689,454 and 3,779,986 that commercial one-component alkoxy-functional RTV systems were obtained. That is, systems that were non-corrosive. However, as was said before, these compositions would not cure at a sufficiently fast rate and did not have good shelf-stability.

Recently, there has been devised a suitable alkoxy-curing, non-corrosive one-component RTV system as disclosed in the patent application of White et al, entitled "One-Package Stable Moisture Curable Polyalkoxy-terminated Organopolysiloxane Compositions, A Method for Making," Ser. No. 277,524, filed on June 26, 1981, now U.S. Pat. No. 4,395,526. Another related disclosure is entitled, "Dialkoxysilanolethers and Method for Making,"—the invention of John E. Hallgren, filed on June 26, 1981, Ser. No. 277,525, now U.S. Pat. No. 4,377,706. The more important disclosure of White et al. discloses the production of non-corrosive, fast-curing one-component RTV compositions by utilizing a scavenger cross-linking agent to absorb and tie up the excess silanol in the polymer in the RTV composition mixture. It is theorized that in the past when alkoxy-functional cross-linking agents were incorporated along with silanol end-stopped polymers in the production of one-component RTV compositions, that even though the composition was dried prior to and after the incorporation of the alkoxy cross-linking agent, there was sufficient hydroxy species such as $H_2O$ methanol present in the polymer mixture to de-stabilize and degrade the polymer mixture such that the desired alkoxy-terminated diorganopolysiloxane linear polymer was obtained in maximum yield. It has also been theorized that the methanol in the polymer attacks the alkoxy groups in the RTV mixture, and degrades such siloxane groups, thus lowering or decreasing the storage stability of the polymer mixture and resulting in the composition being slow curing. Irrespective of whichever of these theories are correct, it has been evidenced that methanol is undesirable in the RTV polymer mixture. It is desirable to have a scavenger in the system which will react with hydroxy groups to produce an unreactive compound which can stay as a filler in the RTV polymer mixture prior, during and after cure of the RTV composition. The functionality of the scavenger can be selected from an oximo, carbamato, enoxy, amino, amido, imidato, and ureido, isocyanato, and thioisocyanato. It should be noted that on page 21, RD-13,275 there is specifically disclosed under Amino Silanes, methyldimethoxy(caprolactamo)silane. However, this is the only cyclic amide that is disclosed in the application as a scavenger cross-linking agent for the non-corrosive RTV system of that application.

Accordingly, there is offered by the present disclosure additional cyclic amide functional scavengers that can be utilized in the production of one-component RTV non-corrosive, low Modulus, fast curing RTV compositions and the methods for preparing the same.

Accordingly, it is one object of the present invention to provide a process for producing a cyclic amide functional RTV scavenger and cross-linking agents.

It is an additional object of the present invention to provide novel cyclic amide functional cross-linking agents as scavenger compounds.

It is still an additional object of the present invention to provide for a one-component RTV system that is non-corrosive, fast curing and has shelf stability, and where the cross-linking agent is an alkoxy-functional silane having a cyclic amide functional scavenging group in the polymer mixture.

It is still an additional object of the present invention to provide for a process for forming a one-component RTV composition which is alkoxy-functional and which is fast-curing, low Modulus, non-corrosive, and shelf stable in which the excess silanol in the polymer is reacted with a cyclic amide functional scavenging agent.

It is still yet an additional object of the present invention to provide for a novel, one-component, non-corrosive fast curing, shelf stable RTV compositions in which the excess silanol in the RTV polymer mixture is reacted with a cyclic amide functional moiety present in the polymer mixture.

These and other objects of the present invention are accomplished by means of the disclosures set forth hereinbelow.

SUMMARY OF THE INVENTION

In accordance with the above objects and as provided by the present invention, there is provided by the present invention, a RTV cross-linking agent as scavenger agent comprised in a compound having the formula

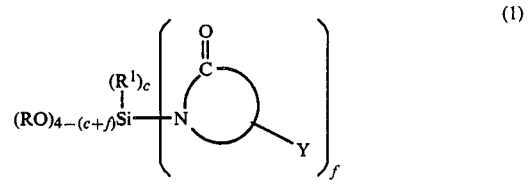

where R is a $C_{(1-8)}$ aliphatic organic radical selected from a group consisting of alkyl, alkylether, alkylester, alkylketone, alkylcyano, and a $C_{(7-13)}$aralkyl radical, $R^1$ is a $C_{(1-13)}$ monovalent substituted or unsubstituted hydrocarbon radical, Y is a

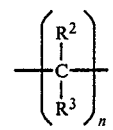

radical where $R^2$, $R^3$ are selected from the class consisting of hydrogen, a $C_{(1-12)}$ alkyl, alkenyl, alkylester, alkylether, aryl, alkaryl and an aralkyl radical, n is a whole number that varies from 2 to 5 and 7, 8, c is a whole number equal to 0 to 3, inclusive, f is an integer equal to 1 to 4 inclusive and the sum of c+f is equal to 1 to 4 inclusive.

There is provided by the present invention a compound having the formula

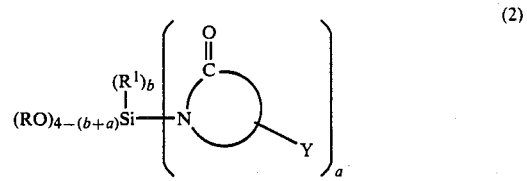

where R is a $C_{(1-8)}$ aliphatic organic radical selected from the group consisting of alkyl, alkylether, alkylester, alkylketone, alkylcyano and a $C_{(7-13)}$ aralkyl radical, $R^1$ is a $C_{(1-13)}$ monovalent substituted or unsubstituted hydrocarbon radical, Y is a

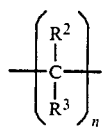

radical, where $R^2$, $R^3$ are selected from the class consisting of hydrogen, a $C_{(1-12)}$ alkenyl, alkyl, alkylester, alkylether, aryl, alkaryl and a aralkyl radical, n is an integer that varies from 2 to 4 and 6, 7 and 8, a is an integer equal to 1 to 2 inclusive, b is a whole number equal to 0 to 1 inclusive, and the sum of b+c is equal to 1 to 2 inclusive.

There is also accomplished by the present invention a process for producing a novel RTV cross-linking agent and compound of the formula,

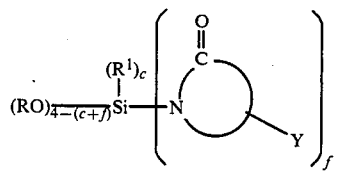
(3)

comprising reacting a silane of the formula,

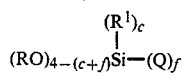
(4)

with a nitrogen compond of the formula,

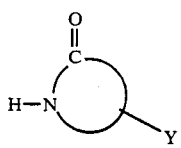
(5)

where R is a $C_{(1-8)}$ aliphatic organic radical selected from the groups consisting of alkyl, alkylether, alkylester, alkylketone, alkylcyano, and a $C_{(7-13)}$ aralkyl radical, $R^1$ is a $C_{(1-13)}$ monovalent substituted or unsubstituted hydrocarbon radical, Y is a

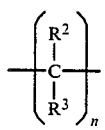

radical where $R^2$, $R^3$ are selected from the class consisting of hydrogen, a $C_{(1-12)}$ alkyl, alkenyl, alkylester, alkylether, arylalkaryl and a aralkyl radical, n is an integer that varies from 2 to 8, Q is a hydrolyzable radical, c is a whole number equal to 0 to 3 inclusive, f is an integer equal to 1 to 4 inclusive, and the sum of c+f is equal to 1 to 4 inclusive.

There is also envisioned by the present invention, a cross-linking agent and scavenger compound having the formula,

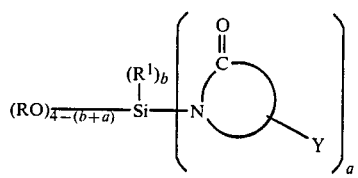
(6)

which is obtained by reacting a silane compound of the formula,

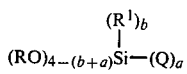
(7)

with a nitrogen compound of the formula,

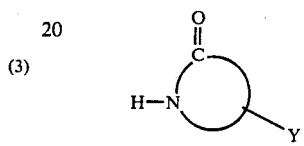
(8)

where R is a $C_{(1-8)}$ aliphatic organic radical selected from the group consisting of alkyl, alkylether, alkylester, alkylketone, alkylorgano and a $C_{(7-13)}$ aralkyl radical, $R^1$ is a $C_{(1-13)}$ monovalent substituted or unsubstituted hydrocarbon radical, Y is a

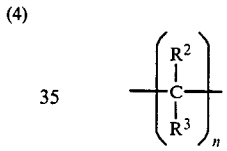

radical, where $R^2$, $R^3$ are selected from the class consisting of hydrogen, a $C_{(1-12)}$ alkyl, alkenyl, alkylester, alkylether, aryl, and a aralkyl radical, n is an integer that varies from 2 to 8, a is an integer equal to 1 to 2 inclusive, b is a whole number equal to 0 to 1 inclusive, and the sum of b+a is equal to 1 to 2 inclusive.

It is also envisioned within the scope of the present invention the RTV compositions obtained by incorporating the foregoing scavenger and cross-linking agents in the RTV compositions which can be disclosed and claimed in various manners as will be shown below.

DESCRIPTION OF THE PREFERRED EMBODIMENT

The RTV cross-linking and scavenger compound of Formula 1 is the preferred compound. In that formula R is a $C_{(1-8)}$ aliphatic organic radical such as an alkyl radical such as methyl, ethyl, propyl, etc. alkyl ether such as methoxyethyl, alkylester such as ethylaceto, alkylketone such as 3-butanonyl, and alkylcyano such as cyanopropyl and a $C_{(7-13)}$ aralkyl radical such as phenylmethyl etc. The above radicals given for the different groupings of the R radical are just given as exemplary and any radical coming within the definition of the R group having 1 to 8 carbon atoms can be utilized in the compound. In the same way, $R^1$ is a $C_{(1-13)}$ monovalent substituted or unsubstituted hydrocarbon radical such as for instance alkyl radicals such as methyl, ethyl, propyl, cycloalkyl radicals such as cyclohexyl, cycloheptyl, cyclo-octyl, etc., alkenyl radicals such as vinyl allyl, etc. mononuclear radicals such as phenyl, methphenyl, etc., and also phenyl, methyl, phenylethyl, etc.

The radicals can also be substituted with various substituent groups such as for instance halogen, such as for instance the $R^1$ group can be a fluoroalkyl group such as 3-3-3-trifluoropropyl.

In the foregoing Formula 1, Y is a hydrocarbon group which is repeated 2 to 4 and 6, 7 or 8 times within the scope of the instant invention. In that group $R^2$, $R^3$ are selected from the class consisting of hydrogen, alkyl, alkenyl, alkylester, alkylether, aryl, alkaryl, and aralkyl radicals. Such groups are selected from the same groups as given for the R radical, preferably $R^2$ and $R^3$ are hydrogen or methyl. It is important to note that n in the carbon chain is present in the heterogenic ring varies from 2 to 4 and 6, 7 to 8. In the formula c, f varies such that there may be up to three of the $R^1$ groups and there may be 1 to 4 of the heterogenic ring groups. The number of alkoxy groups may vary from 1 to 3 inclusive. A preferred compound within the scope of Formula 1 is one of Formula 2. This compound which is within the scope of the compound of Formula 1 the difference is the number that can be present of $R^1$, RO groups and the heterogenic ring groups. In this formula, the nitrogen ring groups may be present in a concentration of 1 to 2 per molecule, the $R^1$ groups may be 0 or 1 and there may be present at least one alkoxy group in the molecule. In the preferred cross-linking agent, there are at least two alkoxy groups present in the molecule. As will be explained below when the scavenger and cross-linking agent meets with the base silanol polymer, the resulting polymer will have at least 2 alkoxy groups in the terminal groups of the linear diorgano-RTV polysiloxane polymer. In the foregoing Formula 1, preferably R and $R^1$ are methyl, and c is equal to 1 and f is equal to 1. Further, preferably $R^2$ and $R^3$ are hydrogen and n varies from 2 to 4.

The compound of Formula 1 was used in one-component RTV compositions and is preferably produced by reacting a silane compound of the formula,

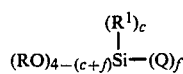
(4)

with a nitrogen compound of the formula,

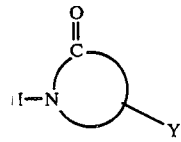
(5)

where R, $R^1$, Y, $R^2$ and $R^3$ are as defined previously, Q is a hydrolyzable radical, c is a whole number equal to 0 to 3 inclusive, f is an integer equal to 1 to 4 inclusive and the sum of c+f is equal to 1 ro 5 inclusive. Preferably, the Q of the hydrolyzable radical is halogen. The reaction proceeds more rapidly when that is the case. The reaction takes place in the presence of an acid acceptor. The acid acceptor can be any primary, secondary and tertiary amine such as for instance, triethylamine, tripropylamine, tributylamine, pyridine, 2,6-lutidine, and N-methyl morpholine. Most preferably, the halogen group is chloro since this type of silane compound is most easily obtained. Preferably, the reaction takes place at a temperature of anywhere from room temperature to 100° C. for 2 to 24 hours, and more preferably from 2 to 12 hours. Most preferably, the reaction is carried out at a temperature varying from room temperature to about 50° C. Preferably the reaction is carried out under pressure although ambient pressures can be utilized. If the reaction is carried out under pressure, then the reaction proceeds at a slightly faster rate.

Most preferably, there is reacted one mole of the nitrogen compound with one mole of a silane, desirably there is utilized a slight excess of the nitrogen compound such as 10 to 15 percent excess so as to get the maximum yield from the process. Also, preferably, the reaction takes place in an organic solvent selected from the class of chlorinated aliphatic solvents such as trichloroethylene, saturated hydrocarbon solvents such as hexane, heptane, octane, etc. and aromatic solvents such as xylene, toluene, etc. and ethers such as diethyl ether, tetrahydrofuran, etc.

After the reaction has proceeded to completion in the foregoing time there is formed as a by-product the acid acceptor salt which precipitates out and is filtered out. The desired product is purified by distillation. It should be noted that the entire reaction takes place in a nitrogen atmosphere since the scavenger groups will react with atmospheric moisture to hydrolyze the scavenger leaving group. Accordingly, it is desirable that the reaction take place under a nitrogen atmosphere and that the cross-linking agent be packaged in a moisture-free atmosphere and stored as such prior to such being utilized to compound RTV compositions. It should be noted that the silane compound of the formula

(4)

can be obtained by reacting a compound of the formula

(9)

with an alcohol of the formula

ROH (10)

where R, $R^1$, Q, c, f are as previously defined and X is a halogen radical. This secondary reaction is one for obtaining the halogen silane compound which is a reactant in the basic process of the instant case and in which some of the halogen groups are substituted by alkoxy groups. This is a straight esterification process whereupon when the halogen is chloro, hydrogen chloride is formed which is removed either by heating the mixture first and then washing it with water or by other known techniques. The resulting desired alkoxylated products of Formula 4 above results basically in about a 60 to 70% yield. A higher yield of such an alkoxylated material may be obtained by a redistribution reaction which is illustrated as follows: Thus, the silane compound of the formula

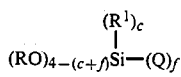 (4)

can be obtained by redistributing a first silane compound of the formula

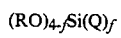 (11)

with a second silane compound of the formula, $(R^1)_c SiQ_{4-c}$ (12)

where Q is halogen, and R, $R^1$, c, and f are as previously defined. Preferably in the above reactions, c and f is equal to 1. In the case where the first silane compound is trialkoxychlorosilane and the second silane compound is monoalkyltrichlorosilane, there is preferably reacted 2 moles of trialkoxychlorisilane with 1 mole of the monoalkyltrichlorosilane so as to get 3 moles of the alkyldialkoxysilane in about 70 to 80% yield. It should be noted that the yield is higher in such a reaction since the entire reaction mixture can be taken and utilized in the reaction with the nitrogen compound to produce the desired scavenger cross-linking agent. That is, if the entire mixture is taken from the above reaction and reacted with a nitrogen compound, then there would be obtained the desired cross-linking scavenger in high yield. This redistribution reaction, is preferably carried out in a time period of anywhere from room temperature to 100° C. and more preferably from 50° to 100° C. for anywhere from 6 to 12 hours.

It should be noted that in the above reaction, the process is general and covers the production of silane compounds such as the silane scavenger and cross-linking agents where the group taken in times is such that it varies anywhere from 2 to 8 times, so as to include with its ambient, the production of methyldiethoxy(caprolactamo)silanes. There is no disclosure of the preparation of such silanes including caprolactamosilanes in the disclosure of White et al, U.S. Pat. No. 4,395,526 or anywhere in the prior art. Accordingly, the process for the production of the silanes of Formula 1 is broader than in the disclosure of the compound itself. It should be noted that in the compounds of Formula 1 when n is equal to 5 and where $R^2$ and $R^3$ are hydrogen the caprolactamosilane is disclosed. Accordingly, even though White et al. discloses caprolactamosilanes, it does not disclose the process for producing them. As noted previously, there is also envisioned that the present invention the cross-linking agent, scavenger compound having the formula

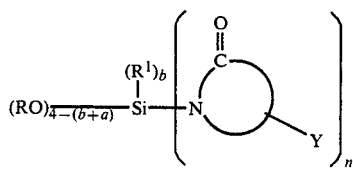 (2)

which is obtained by reacting the silane compound of the formula

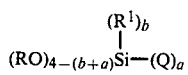 (13)

with a nitrogen compound of the formula,

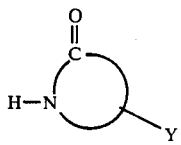 (14)

where R is a $C_{(1-8)}$ aliphatic organic radical selected from the group consisting of alkyl, alkylether, alkylester, alkylketone, alkylorgano and a $C_{(7-13)}$ aralkyl radical, $R^1$ is a $C_{(1-13)}$ monovalent substituted or unsubstituted hydrocarbon radical, Y is a

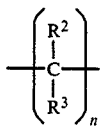

radical where $R^2$, $R^3$ are selected from the class consisting of hydrogen, a $C_{(1-12)}$ alkyl, alkenyl, alkylester, alkylether, aryl, alkaryl and a aralkyl radical, n is an integer that varies from 2 to 8. Accordingly, this is the same process as given previously for the compound of Formula 1 except this is the case where the compound of Formula 1 has the preferred b and a values. Again, the Q may be halogen such as chloro and the alkoxyhalogensilane compound may be obtained either by alkoxylation with an alcohol or by redistribution reaction which is the preferred reaction as discussed above with respect to the process for obtaining the compound of Formula 1. The same reaction conditions apply to these reactions as applied to the reactions utilized to obtain the intermediates which were used to obtain the compounds of Formula 1.

Examples of compounds within the scope of Formulas 1 and 2 are as follows:
Methyldimethoxy-2-pyrrolidonosilane
Methyldiethoxy-2-pyrrolidonosilane
Methylmethoxyethoxy-2-pyrrolidonosilane
Ethyldimethoxy-2-pyrrolidonosilane
Ethyldiethoxy-2-pyrrolidonosilane
Ethylmethoxyethoxy-2-pyrrolidonosilane
Phenyldimethoxy-2-pyrrolidonosilane
Phenyldiethoxy-2-pyrrolidonosilane
Vinyldimethoxy-2-pyrrolidonosilane
Vinyldiethoxy-2-pyrrolidonosilane
Methydimethoxy-2-piperidonosilane
Methyldiethoxy-2-piperidonosilane
Phenyldimethoxy-2-piperidonosilane
Vinyldimethoxy-2-piperidonosilane
Vinyldiethoxy-2-piperidonosilane
Methyldimethoxyl-2-azacyclononanonosilane
Phenyldimethoxy-2-azacyclononanonosilane
Vinyldimethoxy-2-azacyclononanonosilane The cross-linking agent silane compounds of Formula 1 and 2 once obtained can be utilized to produce one-component RTV compositions with advantage. The basic disclosure for this is to be found in the disclosure of White et al, which was referred to previously. Thus, there can be formed a stable one-package substantially anhydrous and substantially acid-free room-temperature vulcanizable composition stable under ambient conditions in the substantial absence of moisture over an extended period of time and converted to a tack-free elastomer comprising: (1) an organopolysiloxane where the silicon atom at each polymer chain end is terminated with at least 2 alkoxy radicals; (2) an effective amount of a condensation catalyst; (3) a stabilizing amount of silane scavenger for hydroxy functional groups having the formula,

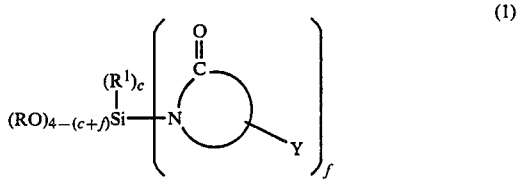
(1)

where R is a $C_{(1-8)}$ aliphatic organic radical selected from the group consisting of alkyl, alkylether, alkylester, alkylketone, and alkylcyano radicals, or a $C_{(7-13)}$ aralkyl radical, $R^1$ is a $C_{(1-13)}$ monovalent substituted or unsubstituted hydrocarbon radical, Y is a

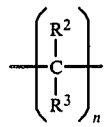

radical where $R^2$, $R^3$ are selected from the class consisting of hydrogen, a $C_{(1-12)}$ alkyl, alkenyl, alkylester, alkylether, aryl, alkenyl and a aralkyl radical, n is a whole number that varies from 2 to 4 and 6, 7, 8 c is a whole number equal to 0 to 3 inclusive, f is an integer equal to 1 to 4 inclusive and the sum of c+f is equal to 1 to 4 inclusive; and (4) an effective amount of a curing accelerator selected from the group consisting of substituted guanidines, amines and mixtures thereof.

The silane can also have Formula 2 above as defined previously. There is also envisioned in the present invention a stable one-compacted substantially anhydrous, acid-free, room-temperature vulcanizable organopolysiloxane composition, stable under ambient conditions in the substantial absence of moisture over an extended period of time and convertible to a tack-free elastomer comprising: (1) an organopolysiloxane wherein the silicon atom at each polymer chain end is terminated with at least 2 alkoxy radicals; (2) an effective amount of a condensation catalyst; (3) a stabilizing amount of a silane scavenger of Formula 1; and (4) an effective amount of a curing accelerator selected from the group consisting of substituted guanidines, amines, and mixtures thereof. Instead of the reactant produced, the invention may be expressed in a slightly different form, that is in terms of the end polymer that is theorized that is substantially formed in the one-component package after the silane scavenger is mixed with the silanol end-stopped diorganopolysiloxane polymer either in the presence or absence of a cross-linking agent. That is in one case, the scavenger may act as both as a cross-linking agent or scavenger and in another case may act only as a scavenger and there may be a separate cross-linking agent in the composition. It can be appreciated that in view of the condensation catalyst and the presence of other ingredients, that not all of the composition may be of the preferred polymer type. However, most of the polymer species should be of this formula, and the formula is of a polyalkoxy terminated organopolysiloxane which has the formula,

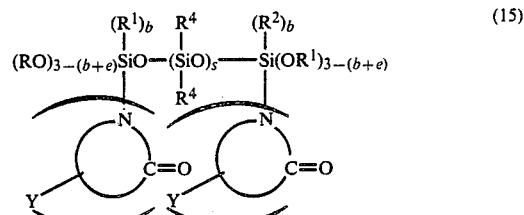
(15)

where $R^4$ is a $C_{(1-13)}$ monovalent substituted or unsubstituted hydrocarbon radical, R is a $C_{(1-8)}$ aliphatic organic radical selected from the group consisting of alkyl, alkylether, alkylester, alkylketone and alkylcyano radicals, or a $C_{(7-13)}$ aralkyl radical, $R^1$ is a $C_{(1-13)}$ monovalent substituted or unsubstituted hydrocarbon radical, Y is a

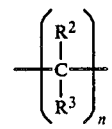

radical selected from the class consisting of hydrogen, a $C_{(1-14)}$ alkyl, alkenyl, alkylester, alkylether, aryl, alkenyl and a aralkyl radical, n is a whole number that varies from 2 to 4, 6, 7,8, and b is a whole number equal to 0 or 1, e is a whole number equal to 0 or 1 inclusive and the sum of b+e is equal to 0 or 1 inclusive, and s is an integer having a value of from about 50 to about 2500 inclusive.

In the case where the one-component RTV composition has a cross-linking agent in addition to the scavenger, then the cross-linking agent may have the formula,

(16)

where R is a $C_{(1-8)}$ aliphatic organic radical selected from the group consisting of alkyl, alkylether, alkylester, alkylketone and alkylcyano radicals, or a $C_{(7-13)}$ aralkyl radical, $R^1$ is a $C_{(1-13)}$ monovalent substituted or unsubstituted hydrocarbon radical, and b is a whole number equal to 0 or 1. It should be noted that R and $R^1$ are as previously defined and can have all the values given previously for R and $R^1$. It should be noted that with respect to compounds of Formula 1, the most preferred silane scavenger is methyldimethoxy-2-pyrrolidonosilane. However, this is just a specific compound and other compounds within the scope of Formulas 1 and 2 can also be utilized in the instant invention.

It should be noted that preferably there is utilized a tin compound as a condensation catalyst. However, more will be said about this later.

In addition there can be utilized an effective amount of a curing accelerator selected from a group consisting of substituted guanidines, amines, and mixtures thereof. Thus, in one respect there is envisioned within the instant invention, an RTV composition which is substantially acid-free and anhydrous, and a stable composition which contains as its basic polymer a polymethoxy-terminated polydimethylsiloxane within the scope of Formula 15 above with an effective amount of a tin condensation catalyst and a stabilizing amount of a polymethoxy-2-pyrrolidonosilane.

There is also envisioned the same composition with a polymethoxy-terminated polydimethylsiloxane and an effective amount of a tin containing condensation catalyst and an effective of a trimethoxysilylpropyltetramethylguanidine curing accelerator and a stabilizing amount of a polymethoxy-2-pyrrolidonosilane. The tin catalyst can be preferably dibutyltindiacetate; however, other tin catalysts can be utilized such as dibutyl tin oxide, dimethyl tin bisneodecanoate and dibutyltindilaurate. There is also envisioned a composition which is curable under ambient conditions an acid-free one-package RTV polyalkoxy composition curable under ambient conditions to a tack-free elastomer over an extended period of time comprising by weight basis 100 parts of a substantially silanol free polysiloxydiorgano siloxy of the Formula 15

(ii) 0 to 10 parts of a cross-linking polyalkoxysilane of the formula

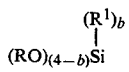

(iii) an effective amount of a condensation catalyst, and (iv) a stabilizing amount of a silane scavenger for hydroxy functional groups having the Formula 1 above where $R^4$ is a $C_{(1-13)}$ monovalent substituted or unsubstituted hydrocarbon radical and R, $R^1$, Y is as previously defined, b is a whole number equal from 0 to 1, a is a whole number equal from 0 to 1 inclusive and the sum of b+e is equal to 0 to 1 inclusive, and s is an integer having a value from 50 to about 2500 inclusive, c is a whole number equal to 0 to 3 inclusive, f is an integer equal to 1 to 4 inclusive, and the sum c+f is equal to 1 to 4 inclusive.

There is also envisioned a RTV composition within the scope of the instant invention, which is acid-free, having as its basic ingredients a polymethoxy-terminated polydimethylsiloxane, a polymethoxysilane cross-linking agent, an effective amount of curing accelerator selected from the group consisting of substituted guanidines, amines, and mixtures thereof, an effective amount of a tin compound condensation catalyst end a stabilizing amount of a silane scavenger selected from the hydroxy groups wherein the hydrolyzable leaving group is a nitrogen group in the compound of Formula 1. In this compound, preferably the polymethoxysilane is methyltrimethoxysilane. The guanidine may be preferably butyltetramethylquanidine or it may be a dialkylamine.

There may also be present in the composition a reinforcing amount of octamethylcyclotetrasiloxane treated silica filler or a silazane treated filler with an effective amount of dibutyltindiacetate condensation catalyst as pointed out previously.

As will be pointed out in more detail, preferably there is utilized an access of up to 3% by weight of a scavenger of Formula 1 or Formula 2 and most preferably a scavenger which is based on the weight of a polydimethylsiloxane of methyldimethoxy-2-pyrrolidonosilane. If based on the weight of the base siloxane polymers, there is preferably utilized an excess of the 3% by weight of the scavenger so as to be sure that it reacts with and absorbs all the silanol groups in the RTV composition mixture. In another aspect of the present invention there is provided a method of making a one-package substantially acid-free, room temperature vulcanizable composition curable to the solid elastomeric state which method comprises agitating under substantially anhydrous conditions at a temperature in the range of from 0° to 180° C. a, a room temperature vulcanizable material selected from a (i) a mixture comprising
(a) 100 parts of a silanol-terminated polydiorganosiloxane consisting essentially of chemically combined units of the formula

(b) a stabilizing amount of a silane scavenger for hydroxy functional groups of Formula 2;
(c) 0 to 10 parts of cross-linking silane of Formula 16;
(d) an effective amount of a condensation catalyst; and
(e) 0 to 5 parts of a curing accelerator selected from the group consisting of substituted guanidines, amines and mixtures thereof, and (ii) a mixture comprising
(a) 100 parts of a polyalkoxy-terminated polydiorganosiloxane of Formula 15,
(iii) 0 to 10 parts of a cross-linking silane of the Formula 16,
(iv) an effective amount of a condensation catalyst,
(v) a stabilizing amount of a silane scavenger for hydroxy functional groups having the Formula 1, and
(vi) 0 to 5 parts of a curing accelerator selected from the group consisting of substituted guanidines, amines and mixtures thereof, where $R^4$, R, $R^1$, Y, as previously defined, n is a whole number that varies from 2 to 4 and 6,7 to 8, a is an integer equal to 1 to 2, b is a whole number equal to 0 to 1 and the sum of a+b is equal to 1 to 2, e is a whole number equal to 0 to 1 and the sum of b+c is equal to 0 to 1, s is an integer having a value from about 50 to about 2500 inclusive, the sum of c+f is as previously defined.

There is also envisioned within the present invention a mixture comprising
(a) 100 parts of a silanol terminated polydiorganosiloxane consisting essentially of chemically combined units of the formula

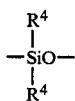

with
(b) a stabilizing amount of a silanol scavenger for hydroxy functional groups of Formula 1;
(c) from 0 to 10 parts of a cross-linking silane of Formula 16;
(d) an effective amount of condensation catalyst;

(e) 0 to 5 parts of a curing accelerator selected from the group consisting of substituted guanidines, amines, and mixtures thereof, where $R^4$, R and $R^1$, Y is as previously defined, n is a whole number that varies from 2 to 5, and 7 to 8, and a is an integer equal from 1 to 2, b is a whole number equal to 0 to 1, and the sum of a+b is equal to 1 to 2.

There is also envisioned within the present invention and a method of making a substantially acid-free room temperature vulcanizable organopolysiloxane composition under substantially anhydrous conditions, the utilizing of an effective amount of a condensation catalyst with an organopolysiloxane with a silicone atom in each polymer chain end and is terminated with at least two alkoxy radicals and improvement which comprises adding to the polyalkoxy terminated organopolysiloxane (1) a stabilized amount of a compound of Formula

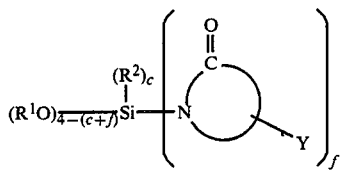

where R is a $C_{(1-18)}$ aliphatic organic radical selected from the group consisting of alkyl, alkylether, alkylester, alkylketone and alkylcyano radicals, or a $C_{(7-13)}$ aralkyl radical, $R^1$ is a $C_{(1-13)}$ monovalent substituted or unsubstituted hydrocarbon radical, Y is a

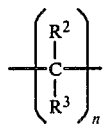

radical where $R^2$, $R^3$ are selected from the class consisting of hydrogen, a $C_{(1-12)}$ alkyl, alkenyl, alkylester, alkylether, aryl, alkaryl and an aralkyl radical, and n is a whole number that varies from 2 to 4 and 6, 7, 8, and c is a whole number equal to 0 to 3 inclusive, f is an integer equal to 1 to 4 inclusive, and the sum of c+f is an integer equal to 1 to 4 inclusive, and (2) an effective amount of a condensation catalyst, whereby improved stability is achieved in the resulting room temperature vulcanizable organopolysiloxane composition.

Preferably, the silanol terminated diorganopolysiloxane has the formula (17)

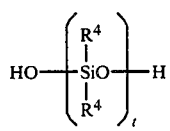

where $R^4$ is a $C_{(1-13)}$ monovalent substituted or unsubstituted hydrocarbon radical, which preferably methyl, or a mixture of a major amount of methyl and a minor amount of phenyl, cyanoethyl, trifluoropropyl, vinyl, and mixtures thereof and t is an integer having a value of from about 50 to about 2500, with a cross-linking silane having hydrolyzable radicals attached to silicon.

As utilized in this application the term "stable" as applied to the one-package polyalkoxy terminated organopolysiloxane RTV's of the present invention, means a moisture curable mixture capable of remaining substantially unchanged while excluded from atmospheric moisture and which cures to a tack-free elastomer after an extended shelf period. In addition, a stable RTV also means that the tack-free time exhibited by freshly mixed RTV ingredients under atmospheric conditions will be substantially the same as that exhibited by the same mixture of ingredients exposed to atmospheric moisture after having been held in a moisture-resistant and moisture-free container for an extended shelf period at ambient conditions, or an equivalent period based on accelerated aging at an elevated temperature.

A study of making of the RTV of the present invention supports the theory of the use of scavening silane of Formula 1 or 2 below or in combinations therefore with cross-linking silane of Formula 16 in accordance with the practice of the invention minimize the likelihood that detrimental amounts of ROH will be generated within the shelf period. Note that ROH generation is to be avoided because ROH end-stopped silanol polymer produces polymers having terminal

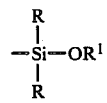

units. These polymers, wherein the silicon atom at each polymer chain is terminated with only one alkoxy radical, have slow cure rates. In addition, ROH can break down the organopolysiloxane polymer in the presence of the condensation catalyst.

The use of the silane scavenger for hydroxy groups in which the leaving group is a nitrogen functional group and is not a halogen radical substantially eliminates undesirable water in the filler and silicone polymer, as well as residual moisture in the RTV composition during the shelf period. In determining what level of silane scavenger of Formula 1 or Formula 2 to be used in the practice of the application, the total hydroxy functionality of the RTV composition can be estimated. The total hydroxy functionality of the polymer can be determined by infrared analysis.

In order to insure that an effective or stabilizing amount of scavenger is used to maintain the stability of the composition over an extended shelf period of six months or more at ambient temperature while in a sealed container, there can be used an additional amount of scavenger over that amount required to endstop the polymer. This excess of scavenger can be up to about 3% by weight, based on the weight of the polymer. The aforementioned 3% of scavenger by weight exceeds that amount required to substantially eliminate available hydroxy functionality in the polymer as a result of reaction between OH functionality and X radicals. In compositions which also contain filler and other additives, the additional amount of scavenger of Formulas 1 or 2 which is required is estimated by running a 48 hour stability check at 100° C. to determine whether the tack-free time remains substantially unchanged as compared to the tack-free time of the composition before aging measured under substantially the same conditions.

Where polyalkoxy-terminated polymer of Formula 15 below is made without using silane scavenger of Formula 1, silane scavenger can be used in the practice of the invention having less than two —OR$^1$ radicals attached to silicon, as shown by the formula,

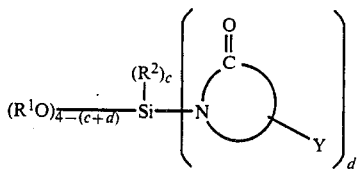 (18)

where R$^1$, R$^2$, and Y are as previously defined, c is a whole number equal to 0 to 3 inclusive, d is an integer equal to 1 to 4 inclusive, and the sum of (c+d) is equal to 3 or 4. In such situations, the scavenging silanes of Formula 18 can be used in an amount sufficient to stabilize the RTV composition as previously defined for the scavenging silane of Formula 1. In addition, there can be used with scavengers of Formulas 1 or 18 at least 0.01 part and up to 10 parts of the cross-linking silane of Formula 16.

The expression "substantially acid-free" with respect to defining the elastomer made from the RTV composition of the present invention upon exposure to atmospheric moisture means yielding by-products having a pKa of 5.5 or greater with 6 or greater preferred and 10 or greater being particularly preferred.

It has been further found that improved cure rates can be achieved if minor amounts of amines, substituted guanidines, or mixtures thereof, are utilized as curing accelerators in the polyalkoxy compositions of the present invention. These curing accelerators also serve to catalyze the ability of the amide leaving group to act as a scavenger. There can be used from 0.1 to 5 parts, and preferably from about 0.3 to 1 part of curing accelerator, per 100 parts of the silanol-terminated polymer of Formula 17, or 100 parts of the polyalkoxy-terminated polymer of Formula 15 to substantially reduce the tack-free time (TFT) of the RTV composition of the present invention. This enhanced cure rate is maintained after it has been aged for an extended shelf period, for example, 6 months or more at ambient temperatures, or a comparable period under accelerated aging conditions. Its cure properties after the extended shelf period will be substantially similar to its initial cure properties, for example, tack-free time (TFT), shown by the RTV composition upon being freshly mixed and immediately exposed to atmospheric moisture.

It appears that the curing accelerators described herein, in addition to decreasing the tack-free times of the RTV compositions of this invention, also provide a surprising stabilizing effect for particular RTV compositions catalyzed with certain condensation catalysts which exhibit a marked lengthening of tack-free time after accelerated aging. For this class of condensation catalysts, addition of amines, substituted guanidines and mixtures thereof described herein provide stable RTV compositions which exhibit a fast cure rate initially, i.e., less than about 30 minutes which remains substantially unchanged after accelerated aging.

The RTV compositions of the present invention can cure to a depth of ⅛" thickness within 24 hours.

Some of the cross-linking polyalkoxysilanes included within Formula 16 are, for example, methyltrimethoxysilane; methyltriethoxysilane; ethyltrimethoxysilane; tetraethoxysilane; vinyltrimethoxysilane; etc.

Among the curing accelerators which can be used in the practice of the invention are silyl substituted guanidines having the formula,

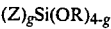

where R is as previously defined, Z is a guanidine radical of the formula,

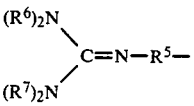

R$^5$ is divalent C$_{(2-8)}$ alkylene radical, R$^6$ and R$^7$ are selected from hydrogen and C$_{(1-8)}$ alkyl radicals and g is an integer equal to 1 to 3 inclusive. In addition, alkyl substituted quanidines having the formula,

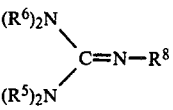

where R$^4$ and R$^5$ are as previously defined and R$^8$ is a C$_{(1-8)}$ alkyl radical, also can be employed. Some of the silyl substituted guanidines included within the above formulas are shown by Takago U.S. Pat. Nos. 4,180,642 and 4,248,993.

In addition to the above-substituted guanidines, there can be used various amines, for example, di-n-hexylamine, hexamethoxymethylamine, and silylated amines, for example, -aminopropyltrimethoxysilane and methyldimethoxy-di-n-hexylaminosilane. Methyldimethoxy-di-n-hexylaminosilane acts as both a scavenger and curing accelerator. The primary amines, secondary amines, silylated secondary amines are preferred, and secondary amines, and silylated secondary amines are particularly preferred. Silylated secondary amines such as alkyldialkoxy-n-dialkylaminosilanes and guanidines such as alkyldialkoxyalkyl-guanidylsilanes which are useful as cure accelerators herein also act as scavengers and, in certain instances, as stabilizers in the compositions of this invention.

Silanol-terminated polydiorganosiloxanes of Formula 17, are well known and preferably have a viscosity in the range of from about 100 to about 400,000 centipoise and more preferred from about 1000 to about 250,000 centipoise when measured at about 25° C. These silanol-terminated fluids can be made by treating a higher molecular weight organopolysiloxane, such as dimethylpolysiloxane with water in the presence of a mineral acid, or base catalyst, to tailor the viscosity of the polymer to the desired range. Methods for making such higher molecular weight organopolysiloxane utilized in the production of silanol-terminated polydiorganosiloxane of Formula 17, or having chemically combined Formula 16A units, also are well known. For example, hydrolysis of a diorganohalosilane such as dimethyldichlorosilane, diphenyldichlorisilane, methylvinyldichlorosilane, or mixtures thereof, can provide for the production of low molecular weight hydrolyzate. Equilibration thereafter can provide for higher molecular weight organopolysiloxane. Equilibration of cyclopolysiloxane such as octamethylcyclotetrasiloxane, octaphenylcyclotextrasiloxane, or mixtures thereof, will also provide for higher molecular weight polymers.

Preferably, such polymers are decatalyzed of equilibration catalyst by standard procedures prior to use, such as shown by Petersen, U.S. Pat. No. 4,125,551, assigned to the same assignee as the present invention.

Silanol-terminated organopolysiloxanes having viscosities below 1200 centipoise can be made by treating organopolysiloxanes consisting essentially of chemically combined diorganosiloxy units with steam under pressure. Other methods that can be employed to make siloanol-terminated polydiorganosiloxanes are more particularly described in U.S. Pat. No. 2,607,792 to Warrick and U.K. Pat. No. 835,790.

Effective amounts of the condensation catalysts which can be used in the practice of the present invention to facilitate the cure of the RTV compositions are, for example, 0.001 to 1 part based on the weight of 100 parts of the silanol-terminated polydiorganosiloxane of Formula 17. There are included tin compounds, for example, dibutyltindilaurate; dibutyltindiacetate; dibutyltindimethyoxide; carbomethoxyphenyl tin tris-uberate; tin octoate; isobutyl tin triceroate; dimethyl tin dibutyrate; dimethyl tin di-neodeconoate; triethyl tin tartrate; dibutyl tin dibenzoate; tin oleate; tin naphthenate; butyltintri-2-ethylhexanoate; tinbutyrate. The preferred condensation catalysts are tin compounds and dibutyltindiacetate is particularly preferred.

Titanium compounds which can be used are for example, 1,3-propanedioxytitanium bis(ethylacetoacetate); 1,3-propanedioxytitanium bis(acetylacetonate); diisopropoxytitanium bis(acetylacetonate); titanium naphthenate; tetrabutyltitanate; tetra-2-ethylhexyltitanate; tetraphenyltitanate; tetraoctadecyltitante; ethyltriethanolaminetitanate. In addition, betadicarbonyltitanium compounds as shown by Weyenberg U.S. Pat. No. 3,334,067 can be used as condensation catalysts in the present invention.

Zirconium compounds, for example, zirconium octoanate, also can be used.

Further examples of metal condensation catalysts are, for example, lead 2-ethyloctanoate; iron 2-ethylhexanoate; cobalt 2-ethylhexanoate; manganese 2-ethylhexanoate; zinc 2-ethylhexanoate; antimony octanoate; bismuth naphthenate; zinc naphthenate; zinc stearate.

Examples of nonmetal condensation catalysts are hexylammonium acetate and benzyltrimethylammonium acetate.

Various fillers and pigments can be incorporated in the silanol or alkoxy-terminated organopolysiloxane, such as for example, titanium dioxide, zirconium silicate, silica aerogel, iron oxide, diatomaceous earth, fumed silica, carbon black, precipitated silica, glass fibers, polyvinyl chloride, ground quartz, calcium carbonate, etc. The amounts of filler used can obviously be caried within wide limits in accordance with the intended use. For example, in some sealant applications, the curable compositions of the present invention can be used free of filler. In other applications, such as the employment of the curable compositions for making binding material on a weight basis, as much as 700 parts or more of filler, per 100 parts of organopolysiloxane can be employed. In such applications, the filler can consist of a major amount of extending materials, such as ground quartz, polyvinylchloride, or mixtures thereof, preferably having an average particle size in the range of from about 1 to 10 microns.

The compositions of the present invention also can be employed as construction sealant and caulking compounds. The exact amount of filler, therefore, will depend upon such factors as the application for which the organopolysiloxane composition is intended, the type of filler utilized (that is, the density of the filler and its particle size). Preferably, a proportion of from 10 to 300 parts of filler, which can include up to about 35 parts of a reinforcing filler, such as fumed silica filler, per 100 parts of silanol-terminated organopolysiloxane is utilized.

In the practice of the invention, the room temperature vulcanizable compositions can be made by agitating, for example stirring, a mixture of materials which can consist of the silanol-terminated polydiorganosiloxane, which hereinafter will include Formula 17 or polymer consisting essentially of Formula 16A units along with the scavenging silane of Formula 1, and cross-linking silane of Formula 16, which can be optional, where the blending is performed in the substantial absence of atmospheric moisture. Thereafter, the condensation catalyst is added also in the substantial absence of atmospheric moisture.

As used hereinafter, the expressions "moisture-free conditions" and "substantially anhydrous conditions," with reference to making the RTV compositions of the present invention, mean mixing in a dry box, or in a closed container which has been subjected to vacuum to remove air, which thereafter is replaced with a dry inert gas, such as nitrogen. Experience has shown that sufficient scavenging silane of Formula 1 should be utilized as previously defined. Temperatures can vary from about 0° C. to about 180° C. depending upon the degree of blending, the type and amount of filler.

A preferred procedure for making the RTV composition of the present invention is to agitate under substantially anhydrous conditions, a mixture of the silanol-terminated polydiorganosiloxane, filler and an effective amount of the scavenging silane of Formula 1 sufficient to effect the substantial elimination of hydroxy functional radicals and to end cap the polymer. This "end capping" and scavenging procedure can require several minutes, hours, or even days, depending upon such factors as the nature of the X leaving group, the number of $-OR^1$ radicals on the scavenging silane, etc. There then can be added to the substantially silanol-free mixture, the condensation catalyst; the cross-linking silane, or mixture thereof, along with other ingredients, for example, the curing accelerator and pigments. A stabilizing excess of the scavenging silane can be used in the initial or final stages of the mixing procedure if desired in amounts previously defined.

In instances where the polyalkoxy-terminated organopolysiloxane of Formula 15 is made by a procedure not requiring the use of scavenging silane of Formula 1, stabilizing amounts of scavenging silane shown by Formulas 2 or 18 can be used. Here, the scavenging silane can be added before, with, or after the addition of condensation catalyst. Alternative procedures for making polyalkoxy-terminated organopolysiloxane are shown as previously indicated by Copper et al, U.S. Pat. No. 3,542,901.

There may be utilized other additives in the instant composition. One of the most noted and preferred type of additives is self-bonding additives, so as to make the composition cure better to various types of substrates such as concrete, various types of masonry substrates, plastic substrates, glass and ceramic substrates and cellulosic substrates. Although the composition of the instant case may have good self-bonding properties to some of the substrates, the self-bonding properties could be improved by the use of self-bonding additives. Accordingly, it is postulated that self-bonding additives of the type disclosed in Mitchell et al, U.S. Pat. No. 4,273,698, can be utilized in the instant case as self-bonding additives in the formulation of self-bonding, one-component RTV compositions. Thus, there may be utilized from 0.1 to 3 parts of weight per 100 parts of the base silanol polymer of self-bonding additives selected from silylmaleates, silyl fumarates, silyl succinates, silyl isocyanurates, silyl cyanurates, as disclosed in the foregoing Mitchell et al patent as self-bonding additives in the instant case to promote the self-bonding properties of the cured composition to various substrates in the absence of a primer. For more details, the worker skilled in the art is referred to the foregoing patent which is hereby incorporated by reference. Other additives can be formulated to be added to the present composition such as flame retardant additives, other types of self-bonding additives, oil-resistant additives, etc.

The examples below are given for the purpose of illustrating the present invention. They are not given for any purpose of setting limits and boundaries to the definition of the instant invention. All parts in the examples are by weight.

EXAMPLE 1

Methyldimethoxy-2-pyrrolidonosilane

To a solution of 1.70 parts (2.0 moles) of 2-pyrrolidone, 220 parts (2.2 moles) of triethylamine, 1500 ml. of toluene, and 1.5 parts of zinc chloride there was added 281 parts (2.0 mole) of methylchlorodimethoxysilane over a period of one hour at room temperature. After stirring at room temperature for an additional 14 hours, triethylaminehydrochlorides were removed by filtration and the filtrates were distilled to give the product, methyldimethoxy-2-pyrrolidonosilane, boiling at 78° C. at 3 mm mercury vacuum.

EXAMPLE 2

The preparation of phenyldimethoxy-2-pyrrolidonosilane

To a reaction vessel there is added 85.1 parts (1.0 moles) of 2-pyrrolidone, 100 parts (1.1 moles) of triethylamine and 800 ml. of toluene. Then to this solution there is added 202.5 parts (1.0 moles) of phenyldimethoxychlorosilane over a period of 50 minutes at room temperature. After stirring at room temperature for an additional 17 hours, triethylaminehydrochloride is removed by filtration. Upon removal and stripping off of the solvent there remains a pale yellow liquid which is phenyldimethoxy-2-pyrrolidonosilane. This example is fictitious.

EXAMPLE 3

This example illustrates the preparation of vinyldimethoxy-2-pyrrolidonosilane

In a reaction vessel containing 85.1 parts (1.0 moles) of 2-pyrrolidone there is added 100 parts (1.1 moles) of triethylamine and 700 ml. of toluene. To this solution there is added 152.5 parts (1.0 moles) of vinyldimethoxychlorosilane over a period of 50 minutes at room temperature. After stirring at room temperature for an additional 17 hours, triethylaminehydrochloride is removed by filtration. Upon removal of the solvent by stripping there is left a liquid which is vinyldimethoxy-2-pyrrolidonosilane. This example is fictitious.

EXAMPLE 4

This example illustrated the preparation of methyldimethoxy-2-piperidonosilane

There is prepared a solution containing 99.1 parts (1.0 moles) of 2-piperidone, 87 parts (1.1 moles) pyridine and 750 ml. of toluene. To this solution there is added over a period of 50 minutes at room temperature 140.5 parts (1.0 moles) of methyldimethoxychlorosilane. After stirring at room temperature for an additional 17 hours, there is removed pyridinehydrochloride by filtration. Upon removal of the solvent by stripping there is left a liquid which is methyldimethoxy-2-piperidonosilane which boils at 78° C. at 3 mm of vacuum pressure. This example is fictitious.

EXAMPLE 5

This example illustrates the preparation of Methyldiethoxy-2-pyrrolidonosilane

There is prepared a solution containing 168.5 grams (1.0 moles) of methyldiethoxychlorosilane; also containing 110.0 parts (1.1 moles) of triethylamine and 700 ml. of toluene. Over a period of 50 minutes at room temperature there is added 85.1 parts (1.0 moles) of 2-pyrrolidone. After stirring at room temperature for an additional 17 hours triethylaminehydrochloride is removed by filtration. Upon removal of the solvent by stripping there is left a liquid methyldiethoxy-2-pyrrolidonosilane. This example is fictitious.

EXAMPLE 6

There was prepared three RTV compositions in accordance with the invention so as to determine their shelf stability. Thus there was prepared Mixture A comprising 100 parts by weight of silanol end-stopped dimethylpolyloxane of 6700 centipoise viscosity at 25° C., 0.25 parts of butyltetramethylguanidine, 0.2 parts of dibutyltindiacetate, and 3.5 parts of methyldimethoxy-2-pyrrolidonosilane. This mixture was mixed under anhydrous conditions in one step that took 15 minutes at room temperature in a SemKit ® mixer.

Then there was prepared a Mixture B comprising 100 parts by weight of silanol end-stopped dimethylpolysiloxane polymer having a viscosity of 6700 centipoise at 25° C., 0.2 parts by weight of dibutyltindiacetate and 3.5 parts by weight of methyldimethoxy-2-pyrrolidonosilane. This mixture was also mixed in a single step for 15 minutes at room temperature under anhydrous conditions in a SemKit ® mixer.

Finally there was prepared a Mixture C comprising 100 parts by weight of a silanol end-stopped dimethylpolysiloxane polymer having a viscosity of 6700 centipoise at 25° C. in which there was mixed 3.5 parts of methyldimethoxy-2-pyrrolidonosilane and 2.5 parts of butyltetramethylguanidine. The three ingredients were first mixed together under anhydrous conditions for 15 minutes at room temperature in a SemKit ® mixer. After this mixture was completed, then in a second mixing step there was added 0.25 parts of dibutyltindiacetate and 1.0 parts of a trimethylsiloxy end-stopped dimethylpolysiloxane polymer having a viscosity of 50 centipoise at 25° C. This second mixture of ingredients was mixed into the first mixture in a second mixing step which took 15 minutes at room temperature under anhydrous conditions in a SemKit ® mixer. The two step mixing process is preferred since it is preferable that the guanidine and the scavenger absorb most of the methanol in the mixture before the dibutyltindiacetate is added to the mixture, since this prevents a viscosity buildup. If this is not done as in the single step mixing then some viscosity buildup in the mixture is experienced. After mixing, Mixtures A, B and C were packed in a sealed aluminum tubes and stored 24 hours at room temperature and 24 hours at 100° C. and 48 hours at 100° C. The storage at the higher temperatures was accelerated shelf aging. Then samples of Mixtures A, B and C were exposed to atmospheric moisture at room temperature to determine the speed and degree of cure as determined by the tack-free-time. A measure of the tack-free-time of the various samples is a measure of storage stability of the RTV mixtures. The results are set forth in Table I below.

TABLE I

| Mixture | Tack-Free-Time (Min) | | | |
|---|---|---|---|---|
| | Initial | 50° C./24 Hrs. | 100° C./24 Hrs. | 100°/48 Hrs. |
| Mixture A | 25 | 10 | 10 | 10 |
| Mixture C | 60 | 15 | 25 | 25 |
| Mixture B | 40 | — | 50 | — |

As the results of Table I indicate, all of the samples had good shelf stability although the two step and the one step mixing with the amine were to be preferred over Mixture B without the amine.

EXAMPLE 7

There was prepared two RTV mixtures with the scavengers of the instant case which were tested to determine the shelf stability of the mixture. The scavenger in this case was methyldimethoxycaprolactamosilane. There was prepared in a one step mixing cycle that took 15 minutes at room temperature under anhydrous conditions a Mixture D comprising 100 parts by weight of a silanol end-stopped dimethylpolysiloxane polymer having a viscosity of 6700 centipoise at 25° C., 3.5 parts by weight of methyldimethoxycaprolactamosilane, 0.3 parts by weight of butyltetramethylguanidine and 0.2 parts by weight of dibutyltindiacetate.

There was prepared a Mixture E in a two step mixing process wherein the first mixture comprised 100 parts by weight of silanol end-stopped dimethylpolysiloxane polymer having a viscosity of 6700 centipoise at 25° C., 3.5 parts by weight of methyldimethoxycaprolactamosilane, 0.3 parts by weight of butyltetramethylguanidine. This first mixture was mixed for 15 minutes at room temperature. Then in a second mixing step there was added to this first mixture 0.2 parts of dibutyltindiacetate and 1.0 parts of a trimethylsiloxy end-stopped dimethylpolysiloxane linear polymer having a viscosity of 50 centipoise at 25° C. This material is a plasticizer and is added to lower the viscosity of the uncured mixture. The second mixing step took 15 minutes time under room temperature and was carried on under anhydrous conditions. Both the one step mixing process and the two step mixing process were carried out in a Sem-Kit ® mixing apparatus. After mixing, Mixtures D and E were packed in sealed aluminum tubes and stored 24 hours at room temperature, for 24 hours at 100° and 48 hours at 100° C. The tack-free-time of the different samples were then determined. In addition, the tack-free-time of samples of the initial material prior to storage was also determined as was the case in Example 6. The results are set forth in Table II below.

TABLE II

| Mixture | Tack-Free-Time (Min) | | | |
|---|---|---|---|---|
| | Initial | R.T./24 Hrs. | 100° C./24 Hrs. | 100° C./79 Hrs. |
| Mixture D | 30 | 25 | 25 | 20 |
| Mixture E | 40 | 35 | 35 | 30 |

The tack-free-time values given in Table II show both samples, that is both Mixtures D and E had good shelf stability; that is, the tack-free-time of the mixture did not unduly increase or decrease after accelerated aging as compared to the tack-free-time of the initial sample. This last Example 7 is given with a compound that is not covered within the composition claims of the instant invention but the example is given nevertheless, to illustrate the reduction to practice of a compound which imparts to the RTV composition the desired shelf stability discussed in this case and the preparation of which compound is covered by the process claims for producing particular pyrrolodino silanes of the present case.

What is claimed is:

1. A stable, one-package, substantially anhydrous and substantially acid-free, room temperature vulcanizable organopolysiloxane compositions stable under ambient conditions in the substantial absence of moisture over an extended period of time and convertible to a tack-free elastomer comprising: (1) an organopolysiloxane wherein the silicon atom at each polymer chain end is terminated with at least 2 alkoxy radicals; (2) an effective amount of a condensation catalyst; (3) a stabilizing amount of silane scavenger for hydroxy functional groups having the formula

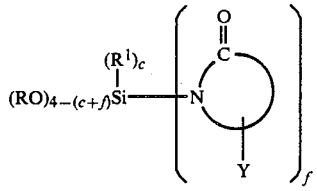

where R is a $C_{(1-8)}$ aliphatic organic radical selected from the group consisting of alkyl, alkylester, alkylketone and alkylcyano radicals, or a $C_{(7-13)}$ aralkyl radical, $R^1$ is a $C_{(1-13)}$ monovalent substituted or unsubstituted hydrocarbon radical, Y is a

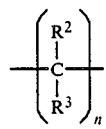

radical, where $R^2$ and $R^3$ are selected from the group consisting of hydrogen, a $C_{(1-12)}$ alkyl, alkenyl, alkylester, alkylether, aryl, alkaryl and a aralkyl radical, n is a whole number that varies from 2 to 4 and 6, 7, 8, c is a whole number equal to 0 to 3 inclusive, f is an integer equal to 1 to 4 inclusive and the sum of c+f is equal to 1 to 4 inclusive.

2. The composition of claim 1, wherein the silane has the formula

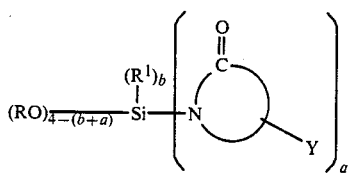

where R is a $C_{(1-8)}$ aliphatic organic radical selected from the group consisting of alkyl, alkylether, alkylester, alkylketone and alkylcyano radicals, or a $C_{(7-13)}$ aralkyl radical, $R^1$ is a $C_{(1-13)}$ monovalent substituted or unsubstituted hydrocarbon radical, Y is a

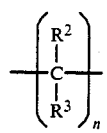

radical where $R^2$ and $R^3$ are selected from the group consisting of hydrogen, a $C_{(1-12)}$ alkyl, alkenyl, alkylester, alkylether, aryl, alkaryl and aralkyl radical, n is a whole number that varies from 2 to 4 and 6, 7, 8, and a is an integer equal to 1 to 2 inclusive, b is a whole number equal to 0 to 1 inclusive, and the sum of b+a is equal to 1 to 2 inclusive and the silane is both the silane scavenger for hydroxy functional groups and a polyalkoxysilane cross-linking agent for terminating the silicon atom at each organopolysiloxane chain end with at least two alkoxy radicals.

3. A stable, one-package, substantially anhydrous and substantially acid-free, room temperature vulcanizable organopolysiloxane composition stable under ambient conditions in the substantial absence of moisture over an extended period of time and convertible to a tack-free elastomer comprising: (1) an organopolysiloxane wherein the silicon atom at each polymer chain end is terminated with at least 2 alkoxy radicals; (2) an effective amount of a condensation catalyst; (3) a stabilizing amount of silane scavenger for hydroxy functional groups having the formula

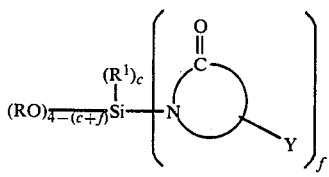

where R is a $C_{(1-8)}$ aliphatic organic radical selected from the group consisting of alkyl, alkylether, alkylester, alkylketone, and alkylcyano radicals, or a $C_{(7-13)}$ aralkyl radical, $R^1$ is a $C_{(1-13)}$ monovalent substituted or unsubstituted hydrocarbon radical, Y is a

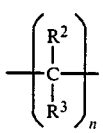

radical where $R^2$ and $R^3$ are selected from the group consisting of hydrogen, a $C_{(1-12)}$ alkyl, alkenyl, alkylester, alkylether, aryl, alkaryl and a aralkyl radical, n is a whole number that varies from 2 to 4 and 6, 7, 8, c is a whole number equal to 0 to 3 inclusive, f is an integer equal to 1 to 4 inclusive and the sum of c+f is equal to 1 to 4 inclusive; and (4) an effective amount of a curing accelerator selected from the group consisting of substituted quanidines, amines and mixtures thereof.

4. A one-package, room temperature vulcanizable polyalkoxy-terminated organopolysiloxane composition in accordance with claim 1, where the polyalkoxy-terminated organopolysiloxane has the formula

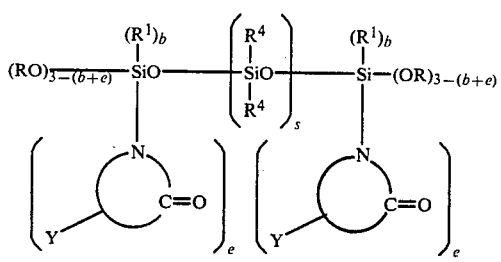

where $R^4$ is a $C_{(1-13)}$ monovalent substituted or unsubstituted hydrocarbon radical, R is a $C_{(1-8)}$ aliphatic organic radical selected from the group consisting of alkyl, alkylether, alkylester, alkylketone and alkylcyano radicals, or a $C_{(7-13)}$ aralkyl radical, $R^1$ is a $C_{(1-13)}$ monovalent substituted or unsubstituted hydrocarbon radical, Y is a

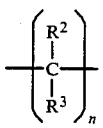

radical where $R^2$ and $R^3$ are selected from the group consisting of hydrogen, a $C_{(1-12)}$ alkyl, alkenyl, alkylester, alkylether, aryl, alkaryl and an aralkyl radical, n is a whole number that varies from 2 to 4, 6, 7, 8, and b is a whole number equal to 0 or 1, e is a whole number equal to 0 or 1 inclusive and the sum of b+e is equal to 0 or 1 inclusive, and s is an integer having a value of from about 50 to about 2500 inclusive.

5. A room temperature vulcanizable composition in accordance with claim 1, having an effective amount of a cross-linking silane of the formula

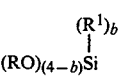

where $R^1$ is a $C_{(1-8)}$ aliphatic organic radical selected from the group consisting of alkyl, alkylether, alkylester, alkylketone and alkylcyano radicals, or a $C_{(7-13)}$ aralkyl radical, $R^1$ is a $C_{(1-13)}$ monovalent substituted or unsubstituted hydrocarbon radical, and b is a whole number equal to 0 or 1.

6. A room temperature vulcanizable composition in accordance with claim 1, where the silane scavenger is methyldimethoxy-2-pyrrolidonosilane.

7. A room temperature vulcanizable composition in accordance with claim 1, which contains a tin compound as the condensation catalyst.

8. A room temperature vulcanizable composition in accordance with claim 4, where $R^4$, R and $R^1$ are methyl and which has a tin compound as a condensation catalyst.

9. A stable, one-package, substantially anhydrous and substantially acid-free, room temperature vulcanizable composition comprising a polymethoxy-terminated polydimethylsiloxane, an effective amount of a tin containing condensation catalyst, and an effective amount of a polymethoxy-2-pyrrolidonosilane scavenger.

10. A stable, one-package, substantially anhydrous and substantially acid-free, room temperature vulcanizable composition comprising a polymethoxy-terminated polydimethylsiloxane, an effective amount of a tin containing condensation catalyst, an effective amount of trimethoxysilylpropyltetramethylguanidine curing accelerator and an effective amount of a polymethoxy-2-pyrrolidonosilane scavenger.

11. A room temperature vulcanizable composition in accordance with claim 9, containing dibutyltindiacetate.

12. A room temperature vulcanizable composition in accordance with claim 9, containing a polymethoxysilane cross-linking agent.

13. A stable and substantially acid-free one-package room temperature vulcanizable polyalkoxy-terminated organopolysiloxane composition curable under ambient conditions to a tack-free elastomer over an extended period of time comprising on a weight basis, (i) 100 parts of a substantially silanol-free polyalkoxysiloxydiorganopolysiloxane of the formula

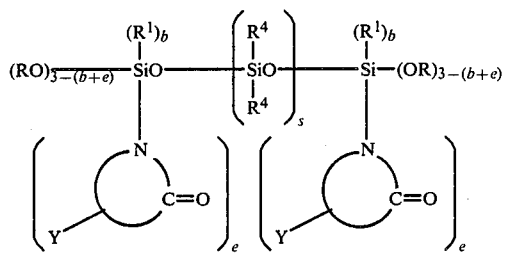

(ii) 0 to 10 parts of a cross-linking polyalkoxysilane of the formula

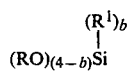

(iii) an effective amount of a condensation catalyst, and (iv) a stabilizing amount of a silane scavenger for hydroxy functional groups having the formula

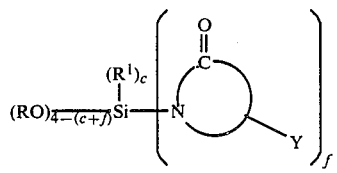

where $R^4$ is a $C_{(1-13)}$ monovalent substituted or unsubstituted hydrocarbon radical, R is a $C_{(1-8)}$ aliphatic organic radical selected from the group consisting of alkyl, alkylether, alkylester, alkylketone, and alkylcyano radicals, or a $C_{(7-13)}$ aralkyl radical, $R^1$ is a $C_{(1-13)}$ monovalent substituted or unsubstituted hydrocarbon radical, Y is a

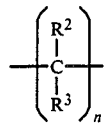

radical where $R^2$ and $R^3$ are selected from the group consisting of hydrogen, a $C_{(1-12)}$ alkyl, alkenyl, alkylester, alkylether, aryl, alkaryl and a aralkyl radical, n is a whole number that varies from 2 to 4 and 6, 7, 8, b is a whole number equal to 0 or 1, e is a whole number equal to 0 to 1 inclusive, and the sum of b+e is equal to 0 or 1 inclusive, and s is an integer having a value of from about 50 to about 2500 inclusive, c is a whole number equal to 0 to 3 inclusive, f is an integer equal to 1 to 4 inclusive and the sum of c+f is equal to 1 to 4 inclusive.

14. A room temperature vulcanizable polyalkoxy-terminated organopolysiloxane composition in accordance with claim 13, containing an effective amount of a curing accelerator selected from the group consisting of substituted quanidines, amines, and mixtures thereof.

15. A one-package room temperatature vulcanizable composition in accordance with claim 13, where $R^4$, R and $R^1$ are methyl.

16. A one-package room temperature vulcanizable composition in accordance with claim 13, where the condensation catalyst is a tin compound.

17. A stable and substantially acid-free, one-package, room temperature vulcanizable composition comprising a polymethoxy-terminated polydimethylsiloxane, a polymethoxysilane, an effective amount of a curing accelerator selected from the group consisting of substituted guanidines, amines and mixtures thereof, an effective amount of a tin compound condensation catalyst, and a stabilizing amount of a silane scavenger for hydroxy functional groups having at least one hydrolyzable leaving group having the formula

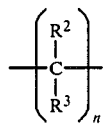

where Y is a

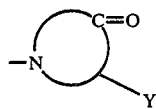

radical, $R^2$ and $R^3$ are selected from the group consisting of hydrogen, $C_{(1-12)}$ alkyl, alkenyl, alkylester, alkylether, aryl, alkaryl and an aralkyl radical, and n is a whole number that varies from 2 to 4 and 6, 7, 8.

18. A one-package room temperature vulcanizable composition in accordance with claim 17, where the polymethoxysilane is methyltrimethoxysilane.

19. A one-package RTV in accordance with claim 17, where the substituted guanidine is butyltetramethylguanidine.

20. A one-package RTV in accordance with claim 17, where the organic amine is a dialkylamine.

21. A substantially acid-free room temperature vulcanizable composition comprising methyldimethoxysiloxy terminated polydimethylsiloxane, a reinforcing amount of octamethylcyclotetrasiloxane treated silica filler, an effective amount of dibutyltindiacetate condensation catalyst, a cure accelerating amount of trimethoxysilylpropyltetramethylguanidine and an excess of up to 3% by weight, based on the weight of the polydimethylsiloxane of methyldimethoxy-2-pyrrolidonosilane.

22. A room temperature vulcanizable composition in accordance with claim 21, having up to 10 parts of methyltrimethoxysilane per 100 parts of the polydimethylsiloxane.

23. A method of making a one-package and substantially acid-free room temperature vulcanizable composition curable to the solid elastomeric state, which method comprises agitating under substantially anhydrous conditions at a temperature in the range of from 0° C. to 180° C., a room temperature vulcanizable material selected from (i) a mixture comprising (a) 100 parts of a silanol-terminated polydiorganosiloxane consisting essentially of chemically, combined units of the formula

(b) a stabilizing amount of a silane scavenger for hydroxy functional groups of the formula

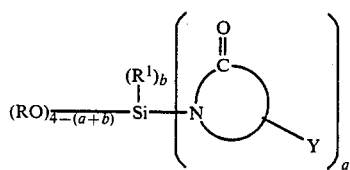

(c) 0 to 10 parts of cross-linking silane of the formula

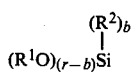

(d) an effective amount of a condensation catalyst, and (e) 0 to 5 parts of a curing accelerator selected from the group consisting of substituted quanidines, amines and mixtures thereof; and (ii) a mixture comprising (a) 100 parts of a polyalkoxy-terminated polydiorganosiloxane of the formula

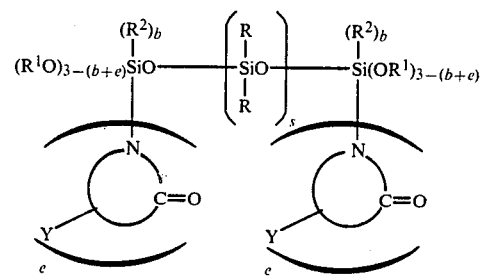

(b) 0 to 10 parts of a cross-linking silane of the formula

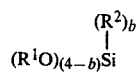

(c) an effective amount of a condensation catalyst, (d) a stabilizing amount of a silane scavenger for hydroxy functional groups having the formula

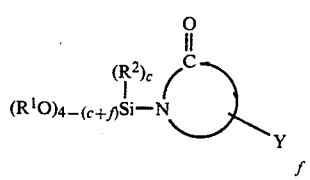

and, (e) 0 to 5 parts of a curing accelerator selected from the group consisting of substituted guanidines, amines and mixtures thereof;

where $R^4$ is selected from $C_{(1-13)}$ monovalent substituted or unsubstituted hydrocarbon radicals, R is a $C_{(1-8)}$ aliphatic organic radical selected from the group consisting of alkyl, alkylether, alkylester, alkylketone and alkylcyano radicals, or a $C_{(7-13)}$ alkaryl radical, $R^1$ is a $C_{(1-13)}$ monovalent substituted or unsubstituted hydrocarbon radical, y is a

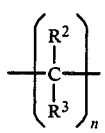

radical where $R^2$, $R^3$ are selected from the class consisting of hydrogen, $C_{(1-12)}$ alkyl, alkenyl, alkylester, alkylether, aryl, alkaryl and an aralkyl radical, n is a whole number that varies from 2 to 4 and 6, 7, 8 and, a is an integer equal to 1 or 2, b is a whole number equal to 0 or 1, and the sum of a+b is equal to 1 or 2, e is a whole number equal to 0 or 1 and the sum of b+e is equal to 0 to 1, s is an integer having a value of from about 50 to about 2500 inclusive, c is a whole number equal to 0 to 3 inclusive, f is an integer equal to 1 to 4 inclusive and the sum of c+f is equal to 1 to 4 inclusive.

24. A method in accordance with claim 23, where $R^4$, R and $R^1$ are methyl.

25. A method in accordance with claim 23, where the curing accelerator is selected from the group consisting of silylated guanidine and alkyl guanidine.

26. A method in accordance with claim 23, where the scavenging silane is a polymethoxy-2-pyrrolidone.

27. A method in accordance with claim 23, where the cross-linking silane is methyltrimethoxysilane.

28. A method in accordance with claim 23, where the condensation catalyst is a tin compound.

29. A mixture comprising
(a) 100 parts of a silanol-terminated polydiorganosiloxane consisting essentially of chemically combined units of the formula

(b) a stabilizing amount of a silane scavenger for hydroxy functional groups of the formula

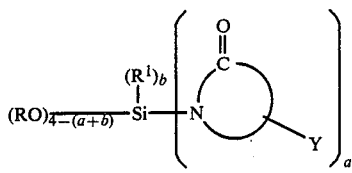

(c) 0 to 10 parts of cross-linking silane of the formula

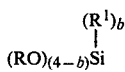

(d) an effective amount of a condensation catalyst, and
(e) 0 to 5 parts of a curing accelerator selected from the group consisting of substituted guanidines, amines and mixtures thereof;
where $R^4$ is selected from $C_{(1-13)}$ monovalent substituted or unsubstituted hydrocarbon radicals, R is a $C_{(1-8)}$ aliphatic organic radical selected from the group consisting of alkyl, alkylether, alkylester, alkylketone and alkylcyano radicals, or a $C_{(7-13)}$ aralkyl radical, $R^1$ is a $C_{(1-13)}$ monovalent substituted or unsubstituted hydrocarbon radical, Y is a

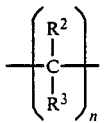

radical where $R^2$ and $R^3$ are selected from the group consisting of hydrogen, a $C_{(1-12)}$ alkyl, alkenyl, alkylester, alkylether, aryl, alkaryl and an aralkyl radical, n is a whole number that varies from 2 to 4 and 6, 7, 8, and a is an integer equal to 1 or 2, b is a whole number equal to 0 or 1, and the sum of a+b is equal to 1 or 2.

30. In the method of making a substantially acid-free room temperature vulcanizable organopolysiloxane composition under substantially anhydrous conditions utilizing an effective amount of a condensation catalyst with a silanol-terminated organopolysiloxane and a polyalkoxysilane cross-linking agent, the improvement which comprises adding to the silanol-terminated organopolysiloxane a stabilizing amount of a polyalkoxysilane which is both a scavenger for hydroxy functional groups and a cross-linking agent of the formula

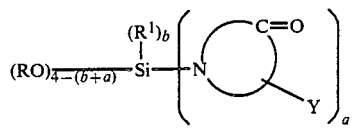

where R is a $C_{(1-8)}$ aliphatic organic radical selected from the group consisting of alkyl, alkylether, alkylester, alkylketone and alkylcyano radicals, or a $C_{(7-13)}$ aralkyl radical, $R^1$ is a $C_{(1-13)}$ monovalent substituted or unsubstituted hydrocarbon radical, Y is a

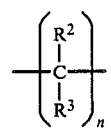

radical, where $R^2$ and $R^3$ are selected from the group consisting of hydrogen, a $C_{(1-12)}$ alkyl, alkenyl, alkylester, alkylether, aryl, alkaryl and an aralkyl radical, and n is a whole number that varies from 2 to 4 and 6, 7, 8, a is an integer equal to 1 or 2, b is an integer equal to 0 or 1, and the sum of a+b is equal to 1 or 2, and thereafter adding an effective amount of a condensation catalyst, whereby improved stability is achieved in the resulting room temperature vulcanizable organopolysiloxane composition.

31. A method in accordance with claim 30, where the silane scavenger is methyldimethoxy-2-pyrrolidonosilane.

32. A method in accordance with claim 30, using an effective amount of dibutyltindiacetate as the condensation catalyst.

33. In the method of making a substantially acid-free room temperature vulcanizable organopolysiloxane composition under substantially anhydrous conditions utilizing an effective amount of a condensation catalyst with an organopolysiloxane wherein the silicon atom at each polymer chain end is terminated with at least two alkoxy radicals, the improvement which comprises adding to said polyalkoxy-terminated organopolysiloxane (1) a stabilizing amount of a silane scavenger for hydroxy functional groups of the formula

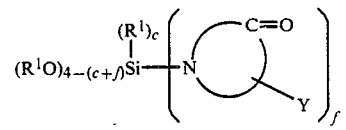

where R is a $C_{(1-8)}$ aliphatic organic radical selected from the group consisting of alkyl, alkylether, alkylester, alkylketone and alkylcyano radicals, or a $C_{(7-13)}$ aralkyl radical, $R^1$ is a $C_{(1-13)}$ monovalent substituted or unsubstituted hydrocarbon radical, Y is a

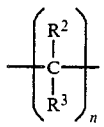

radical where $R^2$ and $R^3$ are selected from the group consisting of hydrogen, a $C_{(1-12)}$ alkyl, alkenyl, alkylester, alkylether, aryl, alkaryl and an aralkyl radical, and n is a whole number that varies from 2–4 and 6, 7, 8, and c is a whole number equal to 0 to 3 inclusive, f is an integer equal to 1 to 4 inclusive, and the sum of c+f is equal to 1 to 4 inclusive, and (2) an effective amount of a condensation catalyst, whereby improved stability is achieved in the resulting room temperature vulcanizable organopolysiloxane composition.

34. A method in accordance with claim 33, where the silane scavenger is methyldimethoxy-2-pyrrolidonosilane.

35. A method in accordance with claim 33, utilizing a stabilizing amount of methyldimethoxy-2-pyrrolidonosilane and an effective amount of methyltrimethoxysilane.

36. A method in accordance with claim 33, using an effective amount of dibutyltindiacetate as the condensation catalyst.

* * * * *